US010539508B2

(12) United States Patent
Suslick et al.

(10) Patent No.: US 10,539,508 B2
(45) Date of Patent: Jan. 21, 2020

(54) PORTABLE DEVICE FOR COLORIMETRIC OR FLUOROMETRIC ANALYSIS, AND METHOD OF CONDUCTING COLORIMETRIC OR FLUOROMETRIC ANALYSIS

(71) Applicant: The Board of Trustees of the University of Illinois, Urbana, IL (US)

(72) Inventors: Kenneth S. Suslick, Champaign, IL (US); Jon R. Askim, Urbana, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 69 days.

(21) Appl. No.: 15/317,840

(22) PCT Filed: Jun. 9, 2015

(86) PCT No.: PCT/US2015/034801
§ 371 (c)(1),
(2) Date: Dec. 9, 2016

(87) PCT Pub. No.: WO2015/191510
PCT Pub. Date: Dec. 17, 2015

(65) Prior Publication Data
US 2017/0102335 A1    Apr. 13, 2017

Related U.S. Application Data

(60) Provisional application No. 62/010,045, filed on Jun. 10, 2014.

(51) Int. Cl.
*G01N 21/78* (2006.01)
*G01N 21/80* (2006.01)
*G01N 21/77* (2006.01)

(52) U.S. Cl.
CPC ............. *G01N 21/78* (2013.01); *G01N 21/80* (2013.01); *G01N 2021/7773* (2013.01);
(Continued)

(58) Field of Classification Search
CPC ............................... G01N 21/78; G01N 21/80
See application file for complete search history.

(56) References Cited

U.S. PATENT DOCUMENTS 5,272,518 A * 12/1993 Vincent .................... G01J 3/12
                                                              250/226
6,372,485 B1    4/2002 Clark et al.
(Continued)

FOREIGN PATENT DOCUMENTS

WO    WO2013/064959 A1    5/2013

OTHER PUBLICATIONS

Preoxidation for Colorimetric Sensor Array Detection of VOCs Hengwei Lin, Minseok Jang, and Kenneth S. Suslick J.Am.Chem. Soc. 2011, 133, 16786-16789 (Year: 2011).*
(Continued)

*Primary Examiner* — Krishnan S Menon
*Assistant Examiner* — Dwan A Gerido
(74) *Attorney, Agent, or Firm* — Brinks Gilson & Lione

(57) ABSTRACT

A portable device for colorimetric or fluorometric analysis comprises a linear array of optically-responsive chemical sensing elements; an image sensor in optical communication with the linear array for determining a spectral response of the optically-responsive chemical sensing elements, where the image sensor comprises at least one light emission source; and electronics connected to the image sensor for analyzing spectral response data. A method of conducting colorimetric or fluorometric analysis comprises exposing a linear array of optically-responsive chemical sensing elements to a fluid comprising an analyte; impinging light on
(Continued)

the linear array and detecting a spectral response of the chemical sensing elements; and determining an exposed color of each of the chemical sensing elements.

13 Claims, 4 Drawing Sheets

(52) U.S. Cl.
CPC ............... *G01N 2021/7786* (2013.01); *G01N 2021/7793* (2013.01); *G01N 2201/0221* (2013.01)

(56) References Cited

U.S. PATENT DOCUMENTS

| | | | |
|---|---|---|---|
| 6,495,102 | B1 | 12/2002 | Suslick et al. |
| 7,261,857 | B2 | 8/2007 | Suslick et al. |
| 7,751,071 | B2 | 7/2010 | Namizuka |
| 2004/0233467 | A1* | 11/2004 | Namizuka ............. G06T 3/4023 358/1.13 |
| 2005/0171449 | A1 | 8/2005 | Suslick et al. |
| 2008/0050839 | A1* | 2/2008 | Suslick .................. A61B 5/083 436/164 |
| 2009/0146080 | A1 | 6/2009 | Liebsch |
| 2010/0166604 | A1 | 7/2010 | Lim et al. |
| 2013/0303929 | A1 | 11/2013 | Martino et al. |

OTHER PUBLICATIONS

Colorimetric sensor arrays: Interplay of geometry, substrate and immobilization Maria K. LaGasse, Jacqueline M. Rankin, Jon R. Askim, Kenneth S. Suslick Sensors and Actuators B 197, 2014, 116-122 (Year: 2014).*

International Search Report and Written Opinion for International PCT No. PCT/US2015/034801, dated Aug. 27, 2015, pp. 1-9.

Bang, Jin Ho et al., "Chemically Responsive Nanoporous Pigments: Colorimetric Sensor Arrays and the Identification of Aliphatic Amines", *Langmuir*, 24 (2008) pp. 13168-13172.

Carey, James R. et al., "Rapid Identification of Bacteria with a Disposable Colorimetric Sensing Array", *J. Am. Chem. Soc.*, 133 (2011), pp. 7571-7576.

Dini, Francesca et al., "Computer screen assisted digital photography", *Sensors and Actuators B*, 179 (2013) pp. 46-53.

Feng, Liang et al., "A colorimetric sensor array for identification of toxic gases below permissible exposure limits", *Chem. Commun.*, 46 (2010) pp. 2037-2039.

Feng, Liang et al., "Colorimetric Sensor Array for Determination and Identification of Toxic Industrial Chemicals", *Anal. Chem.*, 82 (2010) pp. 9433-9440.

Iqbal, Zafar et al., "Classification and quantitative optical analysis of liquid and solid samples using a mobile phone as illumination source and detector", *Sensors and Actuators B*, 185 (2013) pp. 354-362.

Janzen, Michael C. et al., "Colorimetric Sensor Arrays for Volatile Organic Compounds", *Anal. Chem.*, 78 (2006) pp. 3591-3600.

Kemling, Jonathan W. et al., "Nanostructured Substrates for Optical Sensing", *J. Phys. Chem. Lett.*, 2 (2011) pp. 2934-2944.

Kemling, Jonathan W. et al., "Nanoscale porosity in pigments for chemical sensing", *Nanoscale*, 3 (2011) pp. 1971-1973.

Kotesha, N. V. et al., "Development of the colorimetric sensor array for detection of explosives and volatile organic compounds in air", *Proc. of SPIE*, 7673, 767301-1-767301-9.

Lapresta-Fernandez, A. et al., "Environmental monitoring using a conventional photographic digital camera for multianalyte disposable optical sensors", *Analytica Chimica Acta*, 706 (2011) pp. 328-337.

Lapresta-Fernandez, A. et al., "Multi-ion detection by one-shot optical sensors using a colour digital photographic camera", *Analyst*, 136 (2011) pp. 3917-3926.

Lim, Sung H. et al., "A Colorimetric Sensor Array for Detection and Identification of Sugars", *Org. Lett.*, 10, 20 (2008) pp. 4405-4408.

Lim, Sung H. et al., "An optoelectronic nose for the detection of toxic gases", *Nature Chemistry*, 1 (2009) pp. 562-567.

Lim, Sung H. et al., "A colorimetric sensor array of porous pigments", *Analyst*, 134 (2009) pp. 2453-2457.

Lin, Hengwei et al., "A Colorimetric Sensor Array for Detection of Triacetone Triperoxide Vapor", *J. Am. Chem. Soc.*, 132 (2010) pp. 15519-15521.

Lin, Hengwei et al., "Preoxidation for Colorimetric Sensor Array Detection of VOCs", *J. Am. Chem. Soc.*, 133 (2011) pp. 16786-16789.

Musto, Christopher J. et al., "Colorimetric Detection and Identification of Natural and Artificial Sweeteners", *Anal. Chem.*, 81 (2009) pp. 6526-6533.

Musto, Christopher J. et al., "Differential sensing of sugars by colorimetric arrays", *Current Opinion in Chemical Biology*, 14 (2010) pp. 758-766.

Rakow, Neal A. et al., "A colorimetric sensor array for odour visualization", *Nature*, 406 (Aug. 17, 2000) pp. 710-713.

Rakow, Neal A. et al., "Molecular Recognition and Discrimination of Amines with a Colorimetric Array", *Angew. Chem. Int. Ed.*, 44 (2005) pp. 4528- 4532.

Salinas, Yolanda et al., "Monitoring of chicken meat freshness by means of a colorimetric sensor array", *Analyst*, 137 (2012) pp. 3635-3643.

Steiner, Mark-Steven et al., "Chromogenic Sensing of Biogenic Amines Using a Chameleon Probe and the Red-Green-Blue Readout of Digital Camera Images", *Anal. Chem.*, 82, 20 (2010) pp. 8402-8405.

Sen, Avijit et al., "Shape-Selective Discrimination of Small Organic Molecules", *J. Am. Chem. Soc.*, 122 (2000) pp. 11565-11566.

Suslick, Kenneth S. et al., "Seeing Smells: Development of an Optoelectronic Nose", *Quim. Nova*, 30, 3 (2007) pp. 677-681.

Suslick, Kenneth S., "An Optoelectronic Nose: 'Seeing' Smells by Means of Colorimetric Sensor Arrays", www.mrs.org/publications/bulletin, (Oct. 2004) pp. 720-725.

Suslick, Kenneth S. et al., "Colorimetric sensor arrays for molecular recognition", *Tetrahedron*, 60 (2004) pp. 11133-11138.

Suslick, Benjamin A. et al., "Discrimination of Complex Mixtures by a Colorimetric Sensor Array: Coffee Aromas", *Anal. Chem.*, 82 (2010) pp. 2067-2073.

Zhang, Chen et al., "A Colorimetric Sensor Array for Organics in Water", *J. Am. Chem. Soc.*, 127 (2005) pp. 11548-11549.

Zhang, Chen et al., "Colorimetric Sensor Arrays for the Analysis of Beers: A Feasibility Study", *J. Agric. Food Chem.*, 54 (2006) pp. 4925-4931.

Zhang, Chen et al., "Colorimetric Sensor Array for Soft Drink Analysis", *J. Agric. Food Chem.*, 55 (2007) pp. 237-242.

Peter J. Mazzone, MD, MPH, et al., "Exhaled Breath Analysis with a Colorimetric Sensor Array for the Identification and Characterization of Lung Cancer," *Journal of Thoracic Oncology*, vol. 7, No. 1 (Jan. 2012) pp. 137-142.

* cited by examiner

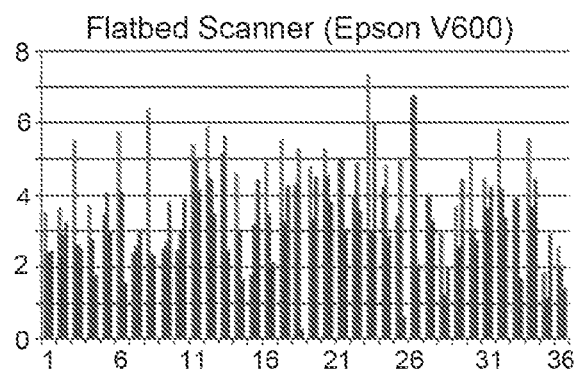
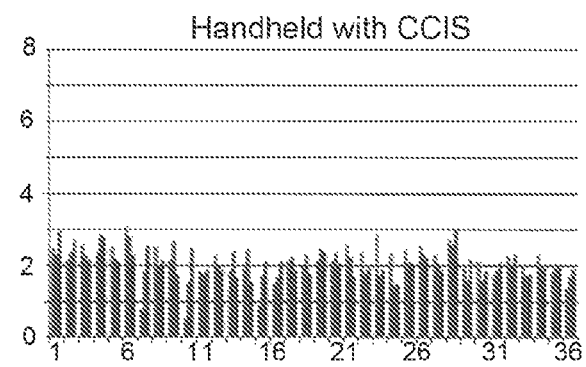
FIGURE 7A       FIGURE 7B
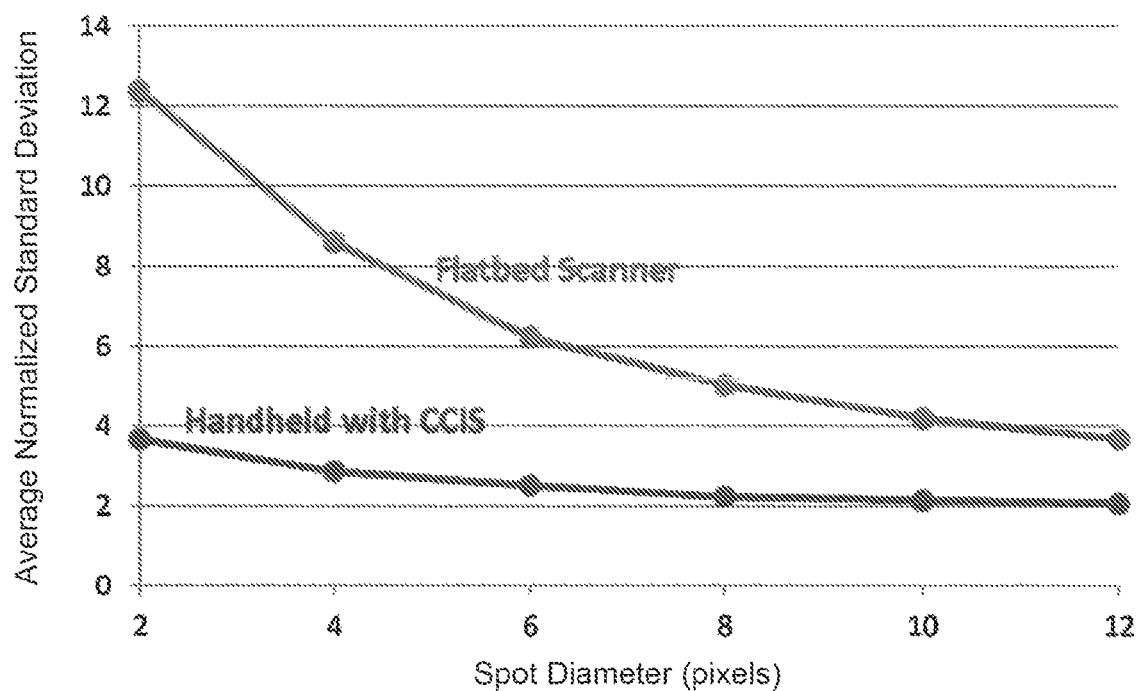
FIGURE 8

PORTABLE DEVICE FOR COLORIMETRIC OR FLUOROMETRIC ANALYSIS, AND METHOD OF CONDUCTING COLORIMETRIC OR FLUOROMETRIC ANALYSIS

RELATED APPLICATIONS

The present patent document is the national stage of International Patent Application No. PCT/US2015/034801, which was filed on Jun. 9, 2015, which claims the benefit of priority under 35 U.S.C 119(e) to U.S. Provisional Patent Application No. 62/010,045, filed on Jun. 10, 2014. Both of these patent documents are hereby incorporated by reference in their entirety.

FEDERALLY SPONSORED RESEARCH OR DEVELOPMENT

This invention was made with government support under contract number Army N41756-12-C-4767 awarded by the Department of Defense, contract number CHE 11-52232 awarded by the National Science Foundation, and contract number PHS 5U01 ES 016011 awarded by the National Institutes of Health. The government has certain rights in the invention.

TECHNICAL FIELD

The present disclosure is related generally to the detection and differentiation of chemical species using colorimetric and/or fluorometric analysis, and more particularly to a portable device for analyzing an optically-responsive chemical sensor array.

BACKGROUND

Array-based sensing has emerged as a potentially powerful tool for the detection of chemically diverse analytes. Based on cross-responsive sensor elements, rather than receptors for specific species, these systems may produce composite responses unique to an odorant, in a fashion similar to the mammalian olfactory system. Previous array detectors for electronic noses have employed a variety of strategies that have generally used weak chemical interactions (e.g., physical adsorption), including the use of conductive polymers and polymer composites, fluorescent dye-doped polymer systems, tin oxide sensors, and polymer coated surface acoustic wave devices. In addition, most approaches to electronic nose technology with cross-reactive sensors have poor chemical selectivity while being extremely sensitive to variations in humidity, a fatal flaw for real-world use.

In contrast to prior electronic nose platforms, two-dimensional colorimetric sensor arrays have a much greater ability to discriminate among similar analytes. A colorimetric sensor may include one or more materials that undergo a change in spectral properties upon exposure to a change in the environment of the sensor. The change in spectral properties may include a change in the absorbance, fluorescence and/or phosphorescence of electromagnetic radiation, including ultraviolet, visible and/or infrared radiation. Since stronger chemical interactions than just physisorption are utilized, the sensitivities of such arrays may be in the few ppb regime, and the arrays may be engineered to be immune to changes in humidity. Current technologies for analyzing two-dimensional colorimetric sensor arrays including flatbed scanners and high resolution cameras that require a computer for data processing.

BRIEF SUMMARY

A portable device for colorimetric or fluorometric analysis comprises a linear array of optically-responsive chemical sensing elements; an image sensor in optical communication with the linear array for determining a spectral response of the optically-responsive chemical sensing elements, where the image sensor comprises at least one light emission source; and electronics connected to the image sensor for analyzing spectral response data.

A method of conducting colorimetric or fluorometric analysis comprises exposing a linear array of optically-responsive chemical sensing elements to a fluid comprising an analyte; impinging light on the linear array and detecting a spectral response of the chemical sensing elements; and determining an exposed color of each of the chemical sensing elements.

The terms "comprising," "containing," "including," and "having" are used interchangeably throughout this disclosure as open-ended terms to refer to the recited elements (or steps) without excluding unrecited elements (or steps).

BRIEF DESCRIPTION OF THE DRAWINGS

FIGS. 7A and 7B show the noise of each spot in a typical flatbed scanner and the prototype handheld device, respectively. The values were normalized to give noise levels relative to the maximum range of the flatbed scanner to account for differences in output range between the two devices (flatbed range: 0-2550; handheld range: 945-2300).

FIG. 8 shows average spot noise in a typical flatbed scanner (top data) and the prototype handheld device (bottom data). As above, the values were normalized to give noise levels relative to the maxium range of the flatbed scanner to account for differences in output range between the two devices (flatbed range: 0-2550; handheld range: 945-2300).

DETAILED DESCRIPTION

A new portable device designed to function as a handheld reader for linear arrays of optically-responsive chemical sensing elements has been developed. The technology may have applications in occupational safety, forensic analysis, environmental monitoring, and in other fields where a colorimetric or fluorometric sensor array could be used to detect or differentiate chemical species.

The portable device uses a linear image sensor (e.g., a color contact image sensor, or CCIS) to read and process a linear array of optically-responsive chemical sensing elements. The sensing elements may be exposed to an analyte passively (e.g., through exposure to ambient air) or actively (e.g., using an onboard pump). For example, a gas or liquid may be pumped over the linear array while the spectral response is monitored by the linear image sensor. The linear array is patterned such that all of the sensor elements can be read by the image sensor in a one-dimensional row of pixels. Software on the device may allow for evaluation of the color or fluorescence changes of the sensor elements over time, allowing for detection and differentiation of chemical species. The color change data may be compared to an onboard library in order to provide instantaneous identification of analytes.

Figure 1:
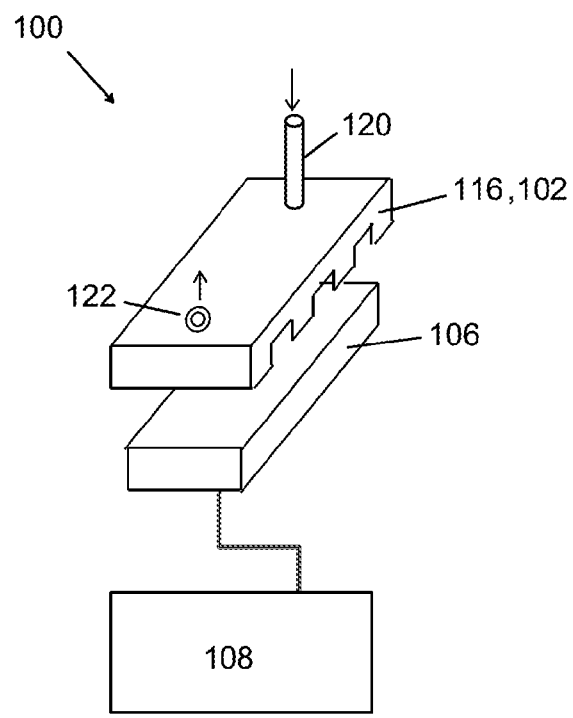
FIG. 1 shows a schematic of an exemplary portable device for analyzing linear arrays of optically-responsive chemical sensing elements.
Figure 2:
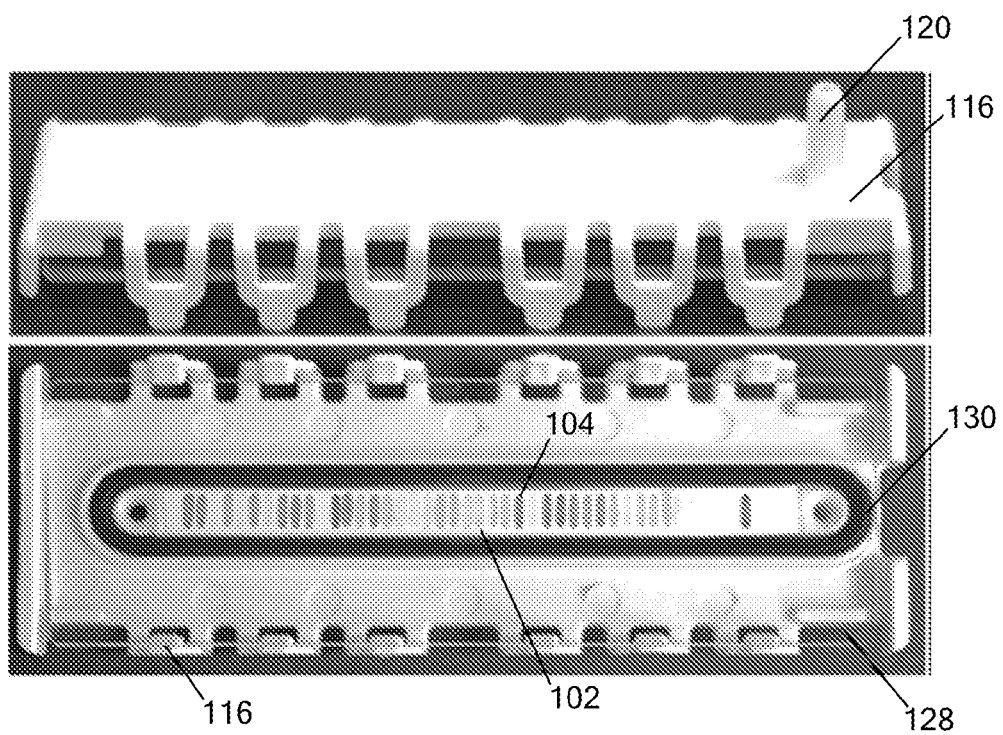
FIG. 2 shows an exemplary cartridge containing a linear array of optically-responsive chemical sensing elements.

Referring to FIGS. 1 and 2, the portable (or handheld) device 100 comprises a linear array 102 of optically-responsive chemical sensing elements 104, and an image sensor 106 positioned in optical communication with the linear array 102 for determining a spectral response of the chemical sensing elements 104. The phrase "in optical communication with" means that the image sensor 106 and the linear array 102 of chemical sensing elements 104 are positioned such that light emitted or reflected from one can reach the other. For example, the image sensor 106 may be positioned opposite and facing the linear array 102, which is mounted in a cartridge 116 as described further below. The image sensor 106 may be a color contact image sensor (CCIS), and the chemical sensing elements 104 of the linear array 102 may comprise one or more chemo-responsive dyes. Electronics 108 are connected to the image sensor 106 for controlling the device and analyzing spectral response data. The electronics 108 may include a complex programmable logic device (CPLD) and a digital signal processor (DSP).

The CCIS or other linear image sensor may include one or more built-in illumination sources and a broadband photo-detector array, which collects data from reflection, absorption, fluorescent and/or phosphorescent events that occur when light impinges on the chemical sensing elements. An exemplary CCIS (M116-A8C1) available commercially from CMOS Sensor Inc. (Cupertino, Calif.) is shown schematically in the cut-away image of FIG. 3 and is described further below. The image sensor may utilize red, green, and blue LEDs as the illumination sources, as shown in the figure. The image sensor may also include one or more other illumination sources that emit a different visible color or non-visible radiation. For example, the other illlumination source may be an orange or amber LED, a near-infrared LED, an ultraviolet LED, or a near-UV LED, all of which are available commercially.

The use of more than three colors (red, green and blue) to probe the linear array may be referred to as "hyperspectral imaging," which may lead to additional spectral information and/or higher color resolution. Thus, modification of a CCIS to allow for hyperspectral imaging may expand the range of colors (or more generally speaking, the electromagnetic wavelengths) probed by the device. The inclusion of near-infrared illumination sources may allow usage of additional types of dyes in the linear array, while the addition of ultraviolet or near-UV light sources may allow for fluorometric or phosphorescent measurement. Fluorescence works by a different method than reflectance or absorption, which are the two electromagnetic response methods typically used with colorimetric sensing elements; however, it is probed in the same manner.

As indicated above, the optically-responsive chemical sensing elements may comprise one or more chemo-responsive dyes that each contain an interaction center to interact strongly with analytes, and the interaction center is preferably strongly coupled to an intense chromophore. The interaction ideally involves stronger chemical interactions than simple physical adsorption. Chemo-responsive dyes can change color, in either reflected or absorbed light, in response to changes in their chemical environment. Among the dye classes that may provide these benefits are (1) Lewis acid/base dyes (i.e., metal on containing dyes), (2) Brensted acidic or basic dyes (i.e., pH indicators), (3) dyes with large permanent dipoles (i.e., solvatochromic dyes), and in many cases, (4) redox responsive dyes, including metal nanoparticle precursors. The disclosures of U.S. Pat. No. 7,261,857 and U.S. Patent Application Publication 2010/0166604, which describe suitable chemo-responsive dyes in greater detail, are hereby incorporated by reference in their entirety.

Linear arrays of optically-responsive chemical sensing elements may be printed using a robotic dip-pin printer, such as the Nanoprint™ LM60 system from Arraylt, a subsidiary of TeleChem International. This machine is believed to be the industry standard in high-throughput micro-array printing. Dip-pin printing is fully compatible with non-aqueous ink/pigment solutions, and printing rates of about 500 arrays per hour may be achieved.

The linear array of optically-responsive chemical sensing elements may comprise a row of discrete spots printed on a substrate, where each of the discrete spots has a linear physical size (e.g., width/length or diameter) of at least 1 pixel. As set forth above, each spot may comprise a chemo-responsive dye. Thus, for an image sensor having a resolution of X dots per inch (dpi), the physical size of each of the discrete spots is preferably at least about 1/X inch or at least about 25.4/X mm. There are typically from 20 to 60 discrete spots in a row. For example, the linear array of optically-responsive chemical sensing elements may take the form of a row of from 28 to 48 discrete spots. Typically, the discrete spots have a center-to-center spacing in the range of from about 1 mm to 1.2 mm. The linear array may also take the form of a continuous line printed on a substrate, where the line has a width of at least 1 pixel, which corresponds to a physical size of at least about 1/X inch, or at least about 25.4/X mm as above. The continuous line may comprise one or more chemo-responsive dyes.

The analysis of the spectral response data collected by the CCIS or other image sensor typically involves averaging over a number of linearly arranged pixels in order to determine the color of a particular chemical sensing element. For example, 5 to 15 linearly arranged pixels may correspond to a discrete spot analyzed as a single chemical sensing element, where edge detection algorithms may help to identify the edges of the spot. Spectral response data from a continuous line of chemo-responsive dye may be analyzed by segmenting the line into a desired number of linearly arranged pixels, where each of these linearly arranged pixels may be considered to be a single chemical sensing element. Alternatively, the averaging may be done over an entire length of the continuous line so that it is analyzed as a single chemical sensing element, if desired.

Figures 4A, 4B:
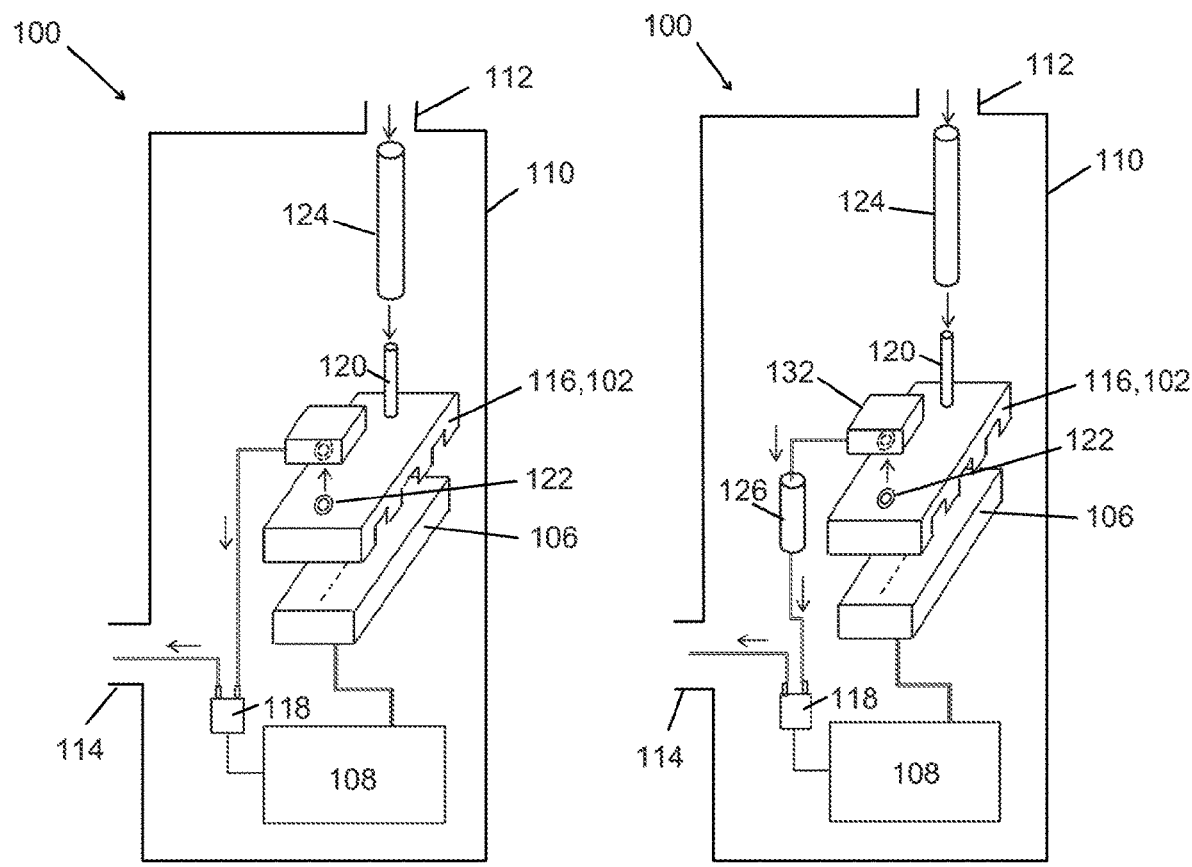
FIGS. 4A and 4B show schematics of the exemplary portable device of FIG. 1 including a housing and additional components.

Referring to FIGS. 4A and 4B, the linear array 102, the color contact image sensor 106 and the electronics 108 may be contained in a housing 110 having an inlet 112 and an outlet 114 for flow of a fluid (gas and/or liquid) comprising the analyte over the linear array 102. Within the housing 110, the linear array 102 of chemical sensing elements 104 may be contained in a sealed cartridge 116 in fluid communication with the inlet 112 and the outlet 114 to the housing 110. The phrase "in fluid communication with" means that fluid passing through the inlet 112 may reach the sealed cartridge 116 (e.g., via a cartridge inlet 120) and fluid passing through the sealed cartridge 116 may reach the outlet 114 (e.g., via a cartridge outlet 122). The portable device 100 may also include an onboard pump 118 for pumping the fluid comprising the analyte through the sealed cartridge 116. To ensure the purity of the analyte, the onboard pump 118 may be configured to pull the fluid containing the analyte through the sealed cartridge 116. To maintain the portability of the device 100, the housing 110 typically has a volume of no greater than about 650 cubic centimeters (40 cubic inches). The sealed cartridge 116 that holds the linear array 102 of chemical sensing elements 104 typically has a volume of from about 15 to 30 cubic centimeters.

Referring again to FIG. 2, the sealed cartridge 116 creates a sealed linear flow channel between an interior surface of the cartridge 116 that may hold the linear array 102 and a cover 128 made of a transparent material, such as a glass slide. The seal 130 itself may be provided by the rubber o-ring that is sandwiched between the cover and the interior surface of the cartridge in a molded groove. In some cases, the linear array may be printed on the glass slide, which may be held in place by a combination of a rubber o-ring and clips molded into the polycarbonate cartridge. Alternatively, the linear array may be printed on a porous membrane (e.g., a polypropylene membrane) attached to the cartridge.

Inlet and outlet ports 120,122 may be molded into the cartridge 116, allowing for connection to a pumping system and/or attachment to sequential or parallel processing units, as described below. The cartridge 116 may therefore control fluid flow over the linear array 102 of sensor elements 104. The cartridge may be designed to work with a liquid medium or a gaseous medium. The cartridge is not limited to a single layout or design, but typically includes a straight channel for fluid flow that allows the chemical sensing elements to be linearly aligned so as to be readable by a linear CCIS. For example, the sealed cartridge may have a length at least 10 times longer than a width thereof due to the one-dimensional nature of the image sensing. The fluid may be flowed through the cartridge at a flow rate (or pump rate) of from about 40 cm$^3$/min to about 600 cm$^3$/min.

The design of the portable reader and cartridge is amenable to the inclusion of other analysis or process technologies in-line with the sensor and flow components, including both pre-processing units and secondary analyzers. For example, referring to FIG. 4A, the portable device may include a pre-processing unit 124 to treat, react with, or modify the chemical nature of the analyte(s) before it reaches the chemical sensing elements read by the image sensor. The pre-processing unit may be in fluid communication with the cartridge inlet 120, for example, so the processing may take place before the analyte reaches the linear array 102. Examples of pre-processing units 124 leading to an array of colorimetric or fluorescent sensors 102 include a pre-oxidation tube or an acid hydrolysis device at the cartridge net 120. Also included in this category is a pre-processing unit 124 configured for phase transduction that would allow, for example, a liquid analyte to be nebulized into a pseudo-gaseous analyte (e.g., a mist carried in a gas stream). In another example, any separation technique (e.g., gas chromatography, liquid chromatography, electrophoresis) may be carded out in a pre-processing unit 124 before the fluid comprising the analyte reaches the linear array 102.

Referring to FIG. 4B, the portable device may also or alternatively comprise a secondary analysis unit 126 in fluid communication with the cartridge outlet 122 (e.g., via a manifold 132) for measurement of one or more characteristics of the analyte after exposure to the chemical sensing elements. In some cases, there may be a parallel analysis unit adjacent to the sealed cartridge between the inlet and the outlet for analysis of a portion of the analyte flowed into the inlet. The secondary analysis unit 126 may provide an alternative set of data on the analyte stream after interaction with the linear array of colorimetric/fluorometric sensing elements. An example of a secondary analyzer 126 is a resistance-measuring semiconducting or metal oxide sensor placed at the outlet 122 of the cartridge 116. Such a sensor could alternatively function as a parallel analysis unit placed in such a way that the fluid containing the analyte is split between the sensor and linear array of chemical sensing elements.

As noted above, the fluid comprising the analyte passed over the linear array may be a gas or a liquid or a combination of a liquid and a gas (e.g., a mist entrained within a gas stream). The gas may be ambient air or a carrier gas that contains the analyte of interest in an amount ranging from 0.1 part per billion to about 100%. The liquid may be an aqueous or organic solvent that comprises the analyte in an amount ranging from 0.1 part per billion to about 100%. In one example, the analyte may be a toxic industrial chemical (TIC), such as ammonia, arsine, chlorine, diborane, dimethylamine, fluorine, formaldehyde, hydrogen chloride, hydrogen cyanide, hydrogen fluoride, hydrogen sulfide, hydrazine, methylamine, methyl hydrazine, nitric acid, nitrogen dioxide, phosgene, phosphine, sulfur dioxide, and/or trimethylamine. In another example, the analyte may be a volatile organic compound (VOC), such as acetaldehyde, formic acid, acetic acid, methanol, ethanol, propanol, benzene, xylene, toluene, nitromethane, ethylene, or propylene.

A method of conducting colorimetric or fluorometric analysis comprises exposing a linear array of optically-responsive chemical sensing elements to a fluid comprising an analyte. The exposure to the fluid may occur for a time duration ranging from about 1 second to about 10 minutes, and more typically from about 1 second to about 1 minute. During and/or after the exposure, light is impinged on the linear array, and a spectral response of the optically-responsive chemical sensing elements is detected. Based on spectral response data, an exposed color of each of the chemical sensing elements may be determined.

A color contact image sensor (CCIS) in optical communication with the linear array may be used to emit the light impinged on the array and detect the spectral response from the chemical sensing elements. The CCIS may include, for example, red, green, and blue LEDs, and optionally additional light sources as described above. A single cycle of light impingement, spectral response detection, and color determination (encompassing each of the chemical sensing elements) may be referred to as a "scan." Depending on the frequency of the scans, the method may enable real-time monitoring. Typically, the scanning occurs at a frequency of from 0 Hz to about 100 Hz, such as from about 0.2 Hz to about 100 Hz. Generally speaking, the frequency may greater than zero (e.g., at least about 0.1 Hz) and is typically about 50 Hz or less, about 20 Hz or less, or about 2 Hz or less.

The method may also entail, before exposing the linear array to the fluid including the analyte, determining a pre-exposure color of each of the chemical sensing elements. Prior to contact with the analyte, light may be impinged upon the linear array and a spectral response of the chemical sensing elements may be detected. As described above, a CCIS or another suitable linear image sensor may be used for the light emission and detection. Using the spectral response data obtained before analyte exposure, a pre-exposure color of each of the chemical sensing elements may be determined. The spectral response data may be obtained in air or in a pure carrier gas or liquid (e.g., solvent) that does not contain the analyte of interest.

The pre-exposure color may be subtracted from the exposed color to determine a changed color of each of the chemical sensing elements, and a difference map showing the changed color of each of the chemical sensing elements may be produced to provide a visual representation of the effect of the analyte exposure on the linear array. By comparing this information to an onboard library of color change signatures, it may be possible to identify the analyte. Advantageously, the method may be carried out using the portable device described in this disclosure.

A digital signal processor (DSP) may be used to analyze the spectral response data and determine the exposed color and/or the pre-exposure color of the chemical sensing elements. This may be done with a median noise level per element of less than about 0.5% relative to the maximum signal. Analyzing the differences between the exposed color and the pre-exposure color may include quantitative comparison of the digital images before and after exposure to the analyte. Using generic spreadsheet software such as Microsoft® Excel®, a difference map can be obtained by subtracting the numeric values of the first image from the numeric values of the second image. To avoid subtraction artifacts at the periphery of the spots, the center of each spot can be averaged.

The method may further include pre-processing, parallel processing, and/or post-processing steps, as set forth above. For example, prior to exposing the linear array of chemical sensing elements to the analyte, the fluid containing the analyte may be pre-processed by acid hydrolysis, gas separation, phase transduction, pre-oxidation, and/or another technique. Also or alternatively, one or more characteristics (e.g., electrical resistance) of the fluid containing the analyte may be measured after exposing the linear array to the fluid. In some cases, a portion of the fluid comprising the analyte may be flowed through a parallel processing unit (which may be located between the inlet and the outlet adjacent to the sealed cartridge) for parallel analysis of the analyte.

Figure 3:
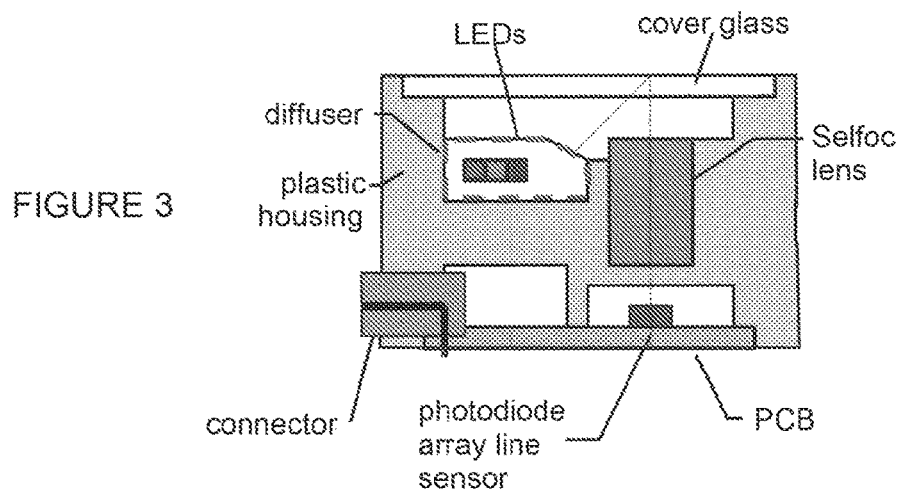
FIG. 3 shows a cut-way view of a commercially-available color contact image sensor (CCIS).

The method may be carried out using the portable device as described above in reference to FIG. 1. The linear array of chemical sensing elements may be contained in a housing having an inlet and outlet for flow of a fluid comprising the analyte therethrough, as shown in FIG. 3. In addition, the linear array may be positioned in a sealed cartridge which is in fluid communication with the inlet and the outlet of the housing. Also as described above, the housing may further include an onboard pump for pumping the fluid comprising the analyte through the sealed cartridge.

Exemplary Portable Device

Figure 5:
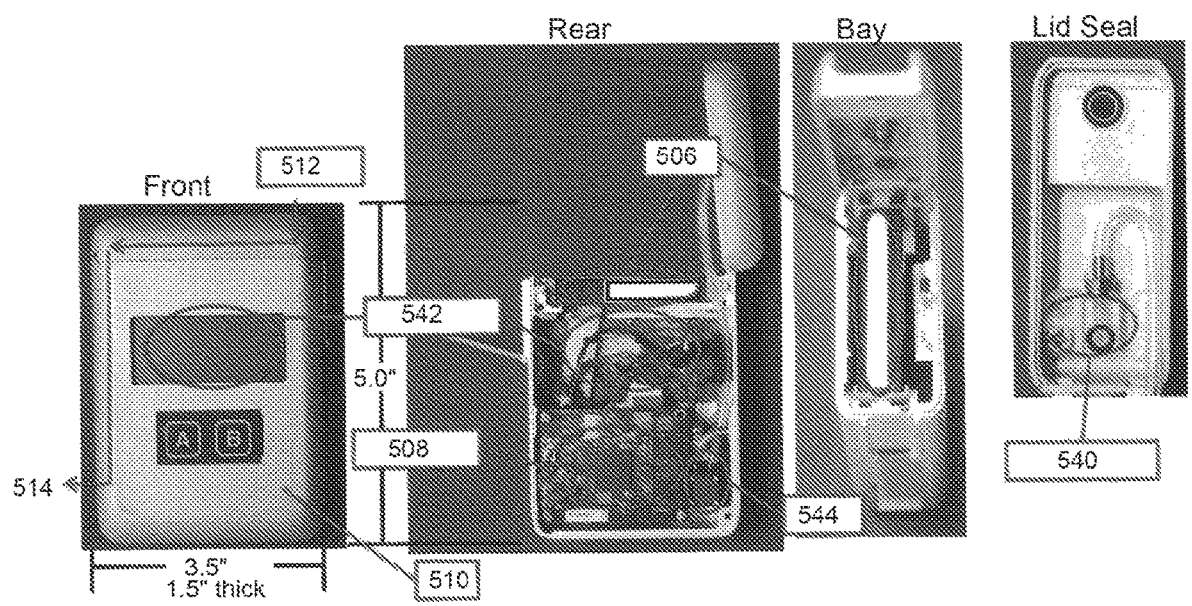
FIG. 5 shows photographs (front, rear, bay and top views) of a fully-functional prototype handheld device disassembled to reveal the components.

Inner components of an exemplary portable device are shown in FIG. 5. On the far left in the figure, the gas flow path through the device is illustrated. The linear array of chemical sensing elements is printed on a cartridge with a snap-seal closure. Examples of suitable individual components of the device are listed in Table 1 below. Table 2 identifies various component parameters of the exemplary portable device.

TABLE 1

Exemplary Individual Components of Portable Handheld Device

| | |
|---|---|
| CCIS 506 | CMOS Sensor, Inc. CCIS M116-A8C1 V01 |
| Electronics 508 | D3 Engineering, Custom (iSense Dauqhter Card Rev A7) |
| Seal manifold 540 | Custom, Clear polycarbonate |
| Housing 510 | Custom, Aluminum |
| LCD display 542 | New Haven Display International, NHD-0420H1Z-FSW-GBW-23231 |
| Diaphragm Micropump 544 | Schwarzer, SP100-EC-LC Art. No. 7S50141 |
| Membrane switches | SSI Electronics, 2 position switch |
| Battery | Tenergy Li-Ion 18650 7.4 V 2200 mAh |
| Cartridge | Custom, White polycarbonate |

TABLE 2

Exemplary Component Parameters of Handheld Reader

| | |
|---|---|
| Scanner Size | 12.8 cm × 9.5 cm × 4.0 cm |
| Scanner Weight | 460 g + battery + cartridge |
| Cartridge Size | 7.9 cm × 2.8 cm × 1.0 cm |
| Battery Weight | 48 g |
| Static Pressure | 550 mbar |
| Pump Rate | 50-580 $cm^3$/min, adjustable |
| Current Draw | ~400 mA at 100% duty |
| Battery Charge | 1200 mAh |
| Scan Time | 11 ms |

Figure 6:
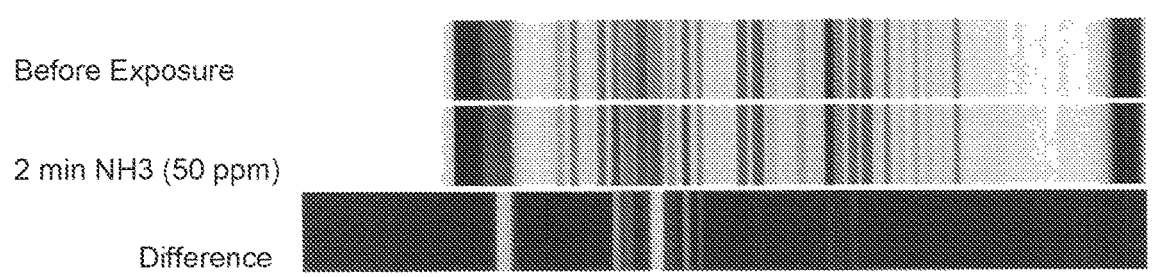
FIG. 6 shows raw images of a linear array of chemical sensing elements before (top) and after (middle) exposure to ammonia, as well as a difference map (bottom) obtained from the data (color difference: 0-466).

FIG. 6 shows several images of an exemplary linear array of chemical sensing elements: The top image shows the appearance of the array before any chemical exposure, the middle image shows the appearance of the array after 2 minutes of exposure to a low level of ammonia (OSHA PEL level, 50 ppm), and the bottom image shows the result of subtracting the top image from the bottom image (note that the color range was expanded for the sake of visibility). In this example, the colored images before and after exposure as well as the difference map were created on a PC from the raw data (integers representing RGB values that typically range between 950 and 3200) collected by the portable device. This analysis may alternatively be done by electronics included on the portable device itself, as described above.

FIGS. 7A and 7B show a spot-by-spot analysis of measurement reproducibility in a typical flatbed scanner in comparison with the exemplary portable device shown in FIG. 5. The portable device shows decreased noise compared to the flatbed scanner, resulting in a signal/noise (and thus detection limit) improvement of a factor of 2-3. This is due to a combination of several factors including scanner motion (the flatbed scanner has a moving sensor bar, while the portable device does not) and improved electronic components. Color variation is independent of spot color (except for very dark spots) in the portable device but is strongly affected by color in the flatbed scanner. Values were normalized to give noise levels relative to the maximum range of the flatbed scanner to account for differences in output range between the two devices (flatbed range: 0-2550; handheld range: 945-2300).

FIG. 8 shows what happens to measurement reproducibility in a typical flatbed scanner and in the portable device as the size of sensing elements changes from 12 pixels in diameter, which is approximately 0.50 mm at a resolution of 600 dpi, to 2 pixels in diameter, which is approximately 0.085 mm at a resolution of 600 dpi. Compared to the flatbed scanner, the portable device shows significantly less noise when analyzing small features. Analysis of small features is important for improvements in miniaturization (whereby sensing elements are made smaller) and improvements in sensitivity (where at especially low concentrations, only a subset of pixels belonging to any given sensor element may respond to the chemical analyte). As above, values were normalized to give noise levels relative to the maximum range of the flatbed scanner to account for differences in output range between the two devices (flatbed range: 0-2550; handheld range: 945-2300).

Referring again to FIG. 3, which shows a cutaway diagram of an exemplary, commercially-available CCIS (M116-ASC1 from CMOS Sensor Inc., Cupertino, Calif.) used in the portable device shown in FIG. 5. The LED light source features an array of LEDs behind a diffuser that converts the array of point-localized sources into a broad, diffuse band that illuminates the entire sensor array; the diffuser is generally very good at eliminating specular reflectance and other nonhomogeneous behavior that could otherwise be expected of an array of point illumination sources. Replacement of any of the three LED arrays as described above with a different wavelength LED is straightforward prior to sealing of the assembly by the manufacturer; likewise, addition of LED arrays (to have, for example, 4 or more separate LED colors) may involve relatively minor engineering modifications. LEDs are readily commercially available from 200 nm to 950 nm, spanning the ultraviolet and visible range and extending into the near-infrared region.

The benefits of the device over previous methods include its portability, rapidity of imaging, sensitivity, and improved signal to noise. The device is very small and light and can be carried in a pocket or on a belt, or placed on a wall in a specific location that requires monitoring. Additionally, the device has much higher scan rates when compared to previous methods, meaning that the device can be used (1) for rapid alarm, (2) for detection of concentration gradients for location of volatile analytes, (3) trace detection through averaging of multiple scans, and (4) measurement of the kinetic development of array response upon initial exposure to analytes. Further, the device exhibits less electronic noise than previous systems and thus may provide increased sensitivity.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A portable device for colorimetric or fluorometric analysis, the device comprising:
a linear array of optically-responsive chemical sensing elements, the linear array consisting of a single linear array;
an image sensor comprising a color contact image sensor (CCIS) in optical communication with the linear array for determining a spectral response of the optically-responsive chemical sensing elements, the image sensor comprising at least one light emission source; and
electronics connected to the image sensor for analyzing spectral response data,
wherein the portable device does not include a moving sensor bar, the image sensor thereby being immovable relative to the linear array of optically-responsive chemical sensing elements.

2. The portable device of claim 1, wherein the optically-responsive chemical sensing elements comprise colorimetric or fluorometric sensing elements.

3. The portable device of claim 1, wherein the electronics comprise a complex programmable logic device (CPLD) and a digital signal processor (DSP).

4. The portable device of claim 1, wherein the single linear array consists of a row of discrete spots, each spot comprising a chemo-responsive dye.

5. The portable device of claim 1, wherein the single linear array consists of a continuous line comprising one or more chemo-responsive dyes.

6. The portable device of claim 1, wherein the at least one light emission source comprises red, green and blue light-emitting diodes.

7. The portable device of claim 6, wherein the image sensor comprises at least one additional light emission source comprising an ultraviolet light emission source or an amber light emission source.

8. The portable device of claim 1, further comprising a housing for containing the linear array, the color contact image sensor and the electronics, wherein the housing includes an inlet and an outlet for flow of fluid comprising an analyte therethrough.

9. The portable device of claim 8, wherein the housing comprises a sealed cartridge in fluid communication with the inlet and the outlet, the sealed cartridge including the linear array of chemical sensing elements.

10. The portable device of claim 9, further comprising an onboard pump for pumping the fluid comprising the analyte through the sealed cartridge.

11. The portable device of claim 9, further comprising a pre-processing unit attached to the sealed cartridge at a cartridge inlet for processing the fluid comprising the analyte before exposure to the chemical sensing elements.

12. The portable device of claim 9, further comprising a secondary analysis unit attached to the sealed cartridge at a cartridge outlet for measurement of one or more characteristics of the fluid comprising the analyte after exposure to the chemical sensing elements.

13. The portable device of claim 9, further comprising a parallel analysis unit adjacent to the sealed cartridge between the inlet and the outlet for parallel analysis of a portion of the fluid comprising the analyte.

* * * * *